(12) United States Patent
Kolkowski et al.

(10) Patent No.: US 8,720,439 B1
(45) Date of Patent: May 13, 2014

(54) HUMIDIFICATION FOR CONTINUOUS POSITIVE AIRWAY PRESSURE SYSTEMS

(75) Inventors: Brian Kolkowski, Leroy, OH (US); Robert N. Schmidt, Cleveland, OH (US); Hani Kayyali, Shaker Heights, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 2444 days.

(21) Appl. No.: 11/505,204

(22) Filed: Aug. 16, 2006

(51) Int. Cl.
*A61M 16/16* (2006.01)

(52) U.S. Cl.
USPC ............ 128/204.21; 128/204.18; 128/203.12

(58) Field of Classification Search
USPC ............ 128/200.16, 200.24, 203.16, 204.14, 128/204.18, 204.21, 204.23, 204.25, 128/204.28, 205.11, 206.21
See application file for complete search history.

(56) References Cited

U.S. PATENT DOCUMENTS

| | | | |
|---|---|---|---|
| 3,990,442 A * | 11/1976 | Patneau | 128/203.16 |
| 4,060,078 A * | 11/1977 | Bird | 128/204.25 |
| 4,083,245 A * | 4/1978 | Osborn | 73/861.53 |
| 4,197,843 A * | 4/1980 | Bird | 128/200.14 |
| 4,323,064 A * | 4/1982 | Hoenig et al. | 128/204.21 |
| 4,327,718 A * | 5/1982 | Cronenberg | 128/205.12 |
| 4,333,451 A * | 6/1982 | Paluch | 128/205.12 |
| 4,340,044 A * | 7/1982 | Levy et al. | 128/204.21 |
| 4,350,646 A | 9/1982 | Baus | |
| 4,944,310 A | 7/1990 | Sullivan | |
| 5,537,996 A | 7/1996 | McPhee | |
| 5,551,419 A * | 9/1996 | Froehlich et al. | 128/204.23 |
| 5,558,084 A | 9/1996 | Daniell | |
| 5,832,176 A | 11/1998 | Jung | |
| 6,041,777 A * | 3/2000 | Faithfull et al. | 128/200.24 |
| 6,363,933 B1 | 4/2002 | Berthon-Jones | |
| 6,557,551 B2 | 5/2003 | Nitta | |
| 6,601,776 B1 | 8/2003 | Oljaca | |
| 6,877,510 B2 | 4/2005 | Nitta | |
| 6,988,498 B2 | 1/2006 | Berthon-Jones | |
| 6,994,083 B2 | 2/2006 | Foley | |
| 7,101,341 B2 * | 9/2006 | Tsukashima et al. | 600/532 |
| 7,290,541 B2 * | 11/2007 | Ivri et al. | 128/200.14 |
| 7,448,376 B2 * | 11/2008 | Lepel | 128/200.14 |
| 2004/0182386 A1* | 9/2004 | Meier | 128/203.12 |
| 2005/0229927 A1* | 10/2005 | Fink et al. | 128/203.12 |
| 2006/0078506 A1* | 4/2006 | Niven et al. | 424/45 |
| 2006/0118111 A1* | 6/2006 | Pelerossi et al. | 128/203.16 |
| 2007/0157931 A1* | 7/2007 | Parker et al. | 128/204.23 |

* cited by examiner

*Primary Examiner* — Loan H Thanh
*Assistant Examiner* — LaToya M Louis
(74) *Attorney, Agent, or Firm* — Brian M. Kolkowski; Robert Knecht Schmidt

(57) ABSTRACT

The present invention encompasses the inclusion of non-heat, active-force humidifiers into CPAP devices. These humidifier modules use for example ultrasonics, atomization, and nebulization to increase the relative humidity of the air being delivered to the patient. Humidity is important in CPAP devices because it is vital to patient comfort and optimum health. All of these various, non-heat active humidifier modules are components or attachments to a CPAP device, and all optionally employ various procedures and devices for dealing with excess condensation. Most importantly, these humidification modules avoid the main problems associated with heat-requiring humidifiers, such as the added cost and time needed to operate these humidifiers, the excess condensation produced, and the increased likelihood of microbial growth.

2 Claims, 7 Drawing Sheets

HUMIDIFICATION FOR CONTINUOUS POSITIVE AIRWAY PRESSURE SYSTEMS

BACKGROUND OF THE INVENTION

1. Field of the Invention

The present invention relates to improved humidification devices for use in continuous positive airway pressure (CPAP) systems. These devices actively humidify air without the need to substantially increase water temperature. The present invention additionally relates to a method for delivering air humidified by non-heat-based humidifiers to airflow delivered to the subject with a CPAP system. The present invention may include a device to collect condensation from the humidified air and recycle the liquid for reutilization in the humidifier.

2. Technical Background

Continuous positive airway pressure (CPAP) devices are used to relieve partial or complete upper airway obstructions in a subject during sleep. A condition known as sleep apnea results when airflow is halted for more than ten seconds during sleep. Sleep apnea leads to decreased blood oxygenation and disrupts sleep. The procedure for administering CPAP treatment has been well documented. An early description can be found in U.S. Pat. No. 4,944,310 (Sullivan). CPAP treatment acts as a pneumatic splint of the airway by applying positive pressure, usually in the range 4 to 20 cm $H_2O$. The air is supplied to the airway by a motor driven blower whose outlet passes via an air delivery hose to a nose and/or mouth mask sealed to a patient's face. An exhaust port is provided in the delivery tube proximate to the mask. CPAP pressure is increased on the detection of pre-defined patterns to provide increased airway pressure to subvert, ideally, the occurrence of the obstructive episodes and the other forms of breathing disorders.

Humidification is an important aspect of the CPAP procedure. The high airflow generated from the CPAP device removes moisture from a subject's nasal cavity, leaving a feeling of dryness and congestion. This dryness is uncomfortable and prevents many users from using the CPAP. In addition to dryness, non-humidified CPAP air may cause bleeding, swelling, excess mucous, congestion, or sneezing. The irritation also creates a very fertile ground for infections. The irritation may be cumulative, building up over time. The only way to reduce the irritation is to add moisture. Humidification therefore can be an important part of CPAP treatment. Besides humidification, water soluble lotions, solutions, or sprays for the nose and prescribed medications such as Nasonex and Flonase can be used to alleviate problems associated with CPAP air.

The prior art includes many references to humidification devices requiring heat (heat-based humidifiers). An example of this is found in U.S. Pat. No. 6,877,510 (Nitta). Heat-based humidifiers, such as heat vaporization humidifiers, heat the liquid as well as the airflow, increasing the maximum amount of water vapor the air can hold. They can also be adjusted to produce more or less moisture by altering the amount of heat applied. Also, the water chamber can be much smaller than in a passive humidifier. An integrated heat-based humidifier, however, cannot be heated as high as a stand-alone heated-based humidifier, due to the close proximity of the heating element to the CPAP. Also, as described below, heat-based humidifiers may produce more condensation than non-heat-based humidifiers, due to a higher temperature difference between the CPAP air and the ambient room temperature. Because of this, these humidifiers are sometimes set at lower constant humidification levels throughout the night, which reduces condensation during the coldest part of the night but prevents optimal humidification at the start and end of the night when temperatures are higher. Other main drawbacks of heat-based humidifiers are that they consume much or more electric power because of the high amount of heat needed to operate, and they require more time to begin humidification than non-heat-based humidifiers because of the need to substantially heat the humidifying liquid. Also, microbial growth is greater in heat-based humidifiers, increasing the risk of patient exposure to, for example, bacteria, yeasts, and molds. Finally, the components of heat-based humidifiers may have to be replaced more often than in non-heat-based humidifiers, as steam canisters need to be replaced every so often and can usually only be purchased from the original manufacturer of the steam humidifier. This increases time and costs associated with maintaining heat-based humidifiers as opposed to non-heat-based humidifiers.

The prior art also describes passive or "passover" humidifiers, which do not require heat. An example of this as integrated into a CPAP device is shown in U.S. Pat. No. 6,827,340 (Austin). These humidifiers are quite simple and, for the most part, self-regulating. They rely on the fact that an air stream passing over a reservoir of liquid or past a wick saturated with that liquid will pick up whatever moisture it can as it "passes over" the liquid. The higher the relative humidity, the harder it is for the air stream to pick up moisture, which is why these humidifiers are self-regulating (as humidity increases the humidifier's water-vapor output naturally decreases due to the decreasing difference in vapor pressure). Although these humidifiers are simple and do not require a heat source, there is no way to increase or decrease the amount of air humidification should this level be too low or high. Also, when integrated into a CPAP device, the surface area of the water used to humidify the air is necessarily smaller, resulting in lower humidification levels. As a result, this humidifier is only feasible in CPAPs set at lower-end pressures, as higher-end pressures will not produce adequate humidification levels. Conversely, increasing the surface area of the water contacting the air will increase the size of the humidifier, to the point where it would be difficult to integrate it into the CPAP. In these cases, the humidifier must be a separate attachment, not part of the CPAP system itself. Also, because of the larger size, these humidifiers may suffer from fill and spill problems because of the large size of the reservoir tank.

Condensation is a problem for any humidifier in a CPAP system. Because the greater the temperature difference between the ambient room temperature and the CPAP air the more condensation is produced, heat-based humidifiers are more susceptible to condensation than other humidifiers, since the air they produce is hotter than air produced in "cold" humidifiers. This is especially a problem at night, when the ambient temperature usually decreases in relation to the temperature of the humidifier. Condensation produces an accumulation of water in the CPAP tubing. This water produces a disruptive gurgling noise and added resistance to the CPAP circuit that results in large, transient fluctuations in mask pressure. Also, as little as 10 ml of condensate can cause an inspiratory pressure drop of up to 5.6 cm $H_2O$. Thus, preventing the formation of condensate in the CPAP tubing is vital to ensuring CPAP therapy remains effective and tolerable. Some CPAP devices with heat-based humidifiers use heated CPAP tubing to prevent condensation, but this can be dangerous. See U.S. Pat. No. 5,537,996 (McPhee). Others use sensors which detect the ambient temperature and adjust heat output accordingly, so that the temperature of the CPAP air is never substantially greater then the temperature of the ambient air, minimizing condensation. See U.S. Pat. No. 5,558,084 (Daniell).

It is an object of the present invention to avoid the drawbacks of heat-based humidifiers and passive humidifiers in CPAP systems. It is further an object of the present invention to produce an integrated, compact, adjustable, cost-effective humidifier for use in CPAP systems. It is even further an object of the present invention to be less susceptible to contaminant growth because it operates at lower temperatures, creating a less hospitable environment for bacteria and other microbes than in heat-based humidifiers. Finally, it is even further an object of the present invention to produce less condensation by operating at temperatures much closer to ambient room temperatures, and through the use of new condensation-removal features in the CPAP device.

SUMMARY OF THE INVENTION

The present invention encompasses the inclusion of non-heat-based, active-force humidifiers into CPAP devices. These humidifier modules use techniques such as for example ultrasonics, atomization, and nebulization to increase the relative humidity of the surrounding air. Humidity is important in CPAP devices because it is vital to patient comfort and optimum health. All of these various, non-heat-based humidifier modules are components of a CPAP device, and all may employ various procedures and devices for dealing with excess condensation. Most importantly, these humidification modules avoid the main problems associated with heat-based humidifiers, such as the added cost and time needed to operate these humidifiers, the excess condensation produced, and the increased likelihood of microbial growth.

Non-heat, active-force humidifiers do not require heat, as distinguished from heat-based (vaporization) humidifiers, and work by applying substantial mechanical force onto a body of water to produce particles small enough for humidification, as distinguished from passive humidifiers. These humidifiers accomplish this active application of mechanical force through various methods, causing the liquid to break up into fine particles, which are then absorbed into the air. In some instances these particles are as small as those in steam. Producing humidification this way produces lower rates of microbial growth and significantly lower energy consumption than, for example, steam humidification, as well as lower maintenance hassles and costs. This process also gives a greater ability to control humidification levels and allows the CPAP device to create a smaller footprint than would be possible using passive humidifiers.

The present invention describes the humidification module device as well as methods for delivering air humidified by that device to the patient. A non-heat-based, active-force humidification module is an integrated component of a CPAP device. The airflow traveling through the CPAP device picks up humidified air from the humidification module before it travels to the subject. Condensation can be eliminated before reaching the mask of the subject through a condensation coil or membrane integrated into the humidification module or through any other method, including adding a reservoir to the CPAP device separate from the humidification module.

Examples of various embodiments of the present invention are as follows. In one embodiment, the present invention includes a continuous positive airway pressure apparatus for treating sleep apneas comprising a device for delivering a pressurized gas to a subject; and a device for actively humidifying a gas and for delivering the humidified gas to the pressurized gas without substantially heating the humidified gas prior to delivery to the subject.

In another embodiment, the present invention includes a method of treating a subject for sleep apneas comprising the steps of actively humidifying a gas without substantially heating a liquid used to humidify the gas; and delivering the humidified gas to a pressurized gas stream prior to delivery of the pressurized gas to a subject.

In yet another embodiment, the present invention includes a continuous positive airway pressure apparatus for treating sleep apneas comprising a device for delivering a pressurized gas to a subject; an ultrasonic humidifier for atomizing a liquid into a gas for creating a humidified gas; and a delivery device for delivering the humidified gas to the pressurized gas prior to delivery to the subject.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENTS

Figure 1:
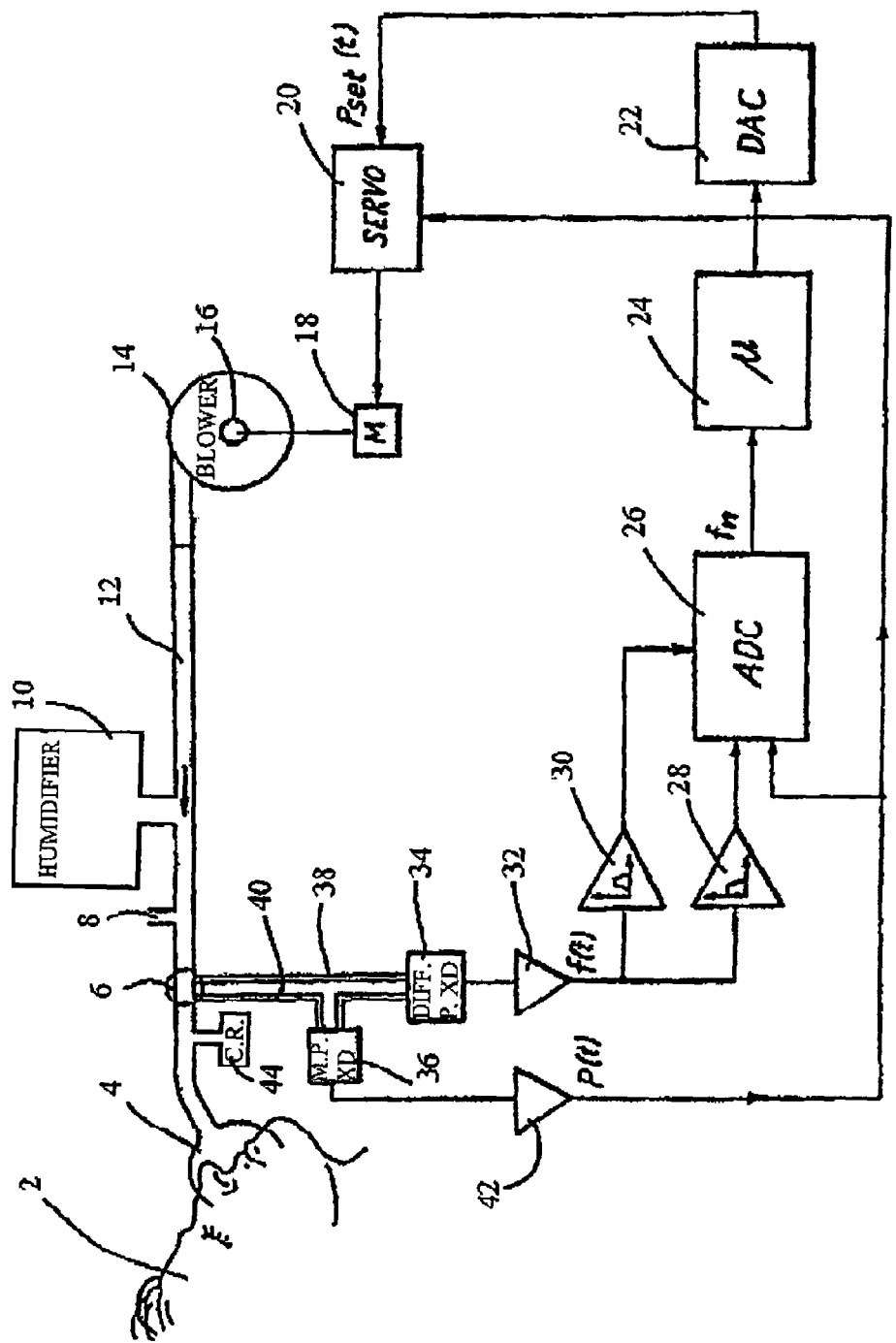
FIG. 1 is a schematic drawing of a preferred embodiment for complete CPAP system, including the attached humidifier and an optional attached condensation reservoir.

FIG. 1 describes a preferred embodiment for a complete CPAP system with active humidification. This system includes the attached non-heat, active humidifier further comprised of a condenser coil for collecting and disposing of condensation before the humidified air reaches the subject. Optionally, the CPAP system may include condensation reservoir separate from the humidifier instead of an attached condensation coil.

In FIG. 1, the subject 2 is wearing a mask 4, preferably the nose mask 4 and/or face mask 4, sealed to his or her face. Breathable gas in the form of fresh air, or oxygen enriched air, enters the mask 4 by flexible tubing 12 which, in turn, is connected to a motor driven blower 14 to which there is provided an air inlet 16. The motor 18 for the blower is controlled by a motor-servo unit 20 to commence, increase or decrease the air pressure supplied to the mask 4 as CPAP treatment. The mask 4 also includes an exhaust port 8 that is close to the junction of the tubing 12 with the mask 4. Exhaust port 8 includes a pressure release valve which releases excess air pressure that exceeds a preset amount. This amount can be adjusted depending on the air pressure needs of the patient.

Interposed between the mask 4 and the exhaust 8 is preferably a linear flow-resistive element 6. In practice, the distance between mask 4 and exhaust 8 is very short so as to minimize deadspace volume. The mask side of the linear flow-resistive element 6 is connected by a small bore tube 40 to a mask pressure transducer 36 and to an input of a differential pressure transducer 34. Pressure at the other side of the flow-resistive element 6 is conveyed to the other input of the differential pressure transducer 34 by another small bore tube 38.

The mask pressure transducer 36 generates an electrical signal in proportion to the mask pressure, which is amplified by amplifier 42 and passed both to a multiplexer/ADC unit 26 and to the motor-servo unit 20. The function of the signal provided to the motor-servo unit 20 is as a form of feedback to ensure that the actual mask static pressure is controlled to be closely approximate to the set point pressure.

The differential pressure sensed across the linear flow-resistive element 6 outputs as an electrical signal from the differential pressure transducer 34, and is amplified by another amplifier 32. The output signal from the amplifier 32 therefore represents a measure of the mask airflow. The linear flow-resistive element 6 can be constructed using a flexible-veined iris. Alternatively, a fixed orifice can be used, in which case a linearization circuit is included in amplifier 42, or a linearization step such as table lookup is included in the operation of controller 24.

The output signal from the amplifier 32 is low-pass filtered by the low-pass filter 28, typically with an upper limit of 10 Hz in order to remove non-respiratory noise. The amplifier 32 output signal is also bandpassed by the bandpass filter 30, typically in the range of 30 to 100 Hz to yield a snoring signal. The outputs from both the low-pass filter 28 and the bandpass filter 30 are provided to the multiplexer/ADC unit 26. The digitized respiratory airflow (FLOW), snore, and mask pressure ($P_{mask}$) signals from multiplexer/ADC 26 are passed to a controller 24, typically constituting a microprocessor based device provided with program memory and data processing storage memory.

The controller 24 outputs a pressure request signal which is converted to a voltage by DAC 22, and passed to the motor-servo unit 20. This signal therefore represents the set point pressure $P_{set(t)}$ to be supplied by the blower 14 to the mask 4 in the administration of CPAP treatment. The controller 24 is programmed to perform a number of processing functions.

This CPAP system is only one of many embodiments of this system, and a number of different variations may be employed to improve efficiency and/or convenience.

Also in FIG. 1 a humidifier 10 is included in the CPAP system by means of the flexible tubing 12 preferably between the linear flow-resistive element 6 and the motor driven turbine 14. The humidifier 10 should be upstream of the linear flow-resistive element 6 for accurate flow measurements. This active humidification module can take one of many forms. Examples of these forms include ultrasonic humidification, atomization, nebulization humidification, and the like. As described above, these techniques work through active, non-heat humidification, which all utilize a means of applying substantial mechanical force to a body or stream of liquid to cause that liquid to disperse into droplets fine enough to humidify the surrounding air.

The humidification devices covered by the present invention are preferably adjustable as to the level of humidification they impart. Further preferably, the relative humidity level of the gas to be humidified can be increased by 10% with respect to the humidity of the ambient air. More preferably, the relative humidity of the gas to be humidified can be increased by 20% with respect to the humidity of the ambient air. Most preferably, the relative humidity of the gas to be humidified can be increased by 30% with respect to the humidity of the ambient air. In a preferred embodiment of the present invention, sensors can be placed to measure the humidification levels of both the humidified gas and the ambient gas in order to determine the humidity difference between these two gases.

Because the humidification devices of the present invention do not require a substantial amount of heat for humidification, they usually produce less condensation. This is due to the larger temperature difference between the heated-water humidified air and the surrounding ambient air, when compared to the air humidified by the present invention. It is more likely that liquid droplets will condense out of the hotter humidified air. Thus, preferably, the temperature of the gas humidified by the present invention is no more than 10° C. warmer than the ambient air temperature. More preferably, the temperature of the gas humidified by the present invention is no more than 5° C. warmer than the ambient air temperature.

Microbial growth is also deterred by the humidification devices of the present invention, since they do not rely on the application of a substantial amount of heat for the humidification process. By keeping the internal temperature of the CPAP apparatus lower, microorganisms such as bacteria, fungi, and molds will not grow as rapidly. Preferably, the CPAP apparatus of the present invention will show 10% less microbial growth over a period of a month than the best devices requiring a substantial amount of heat, or than what is reported in the literature, at the time this application is filed. More preferably, the apparatus will show 20% less microbial growth over a period of a month than the best devices requiring a substantial amount of heat, or than what is reported in the literature, at the time this application is filed. Finally, most preferably, the apparatus will show 30% less microbial growth over a period of a month than the best devices requiring a substantial amount of heat, or than what is reported in the literature, at the time this application is filed.

An ultrasonic humidifier is the preferred humidification device for the present invention. Ultrasonic humidifiers use of high-intensity acoustic energy to alter the properties of liquids, and can turn water into a fine mist through ultrasonic vibrations. Ultrasonic sound is sound with a frequency greater than the upper limit of human hearing (generally above 20 KHz, or 20,000 cycles per second). Ultrasonic humidification, which is an adiabatic type of system, is known for using very little energy (about 7% of the electric usage of electric steam generators). It also provides high-quality moisture and allows close control of the humidification level while requiring little maintenance. Ultrasonic humidification is the preferred way to make a steam size droplet (approximately 1 micron) without having to boil water. An ultrasonic humidifier's initial costs are often much higher than other types of systems, particularly steam systems. Also, it requires very pure water, although smaller systems can use deionized water canisters, which clean the water to approximately 2.5 ppm. While heat vaporization systems may have much lower initial costs, the money spent on replacement parts can be considerable as steam canisters need to be replaced every so often and can usually only be purchased from the original manufacturer. In addition, ultrasonic humidifiers begin humidifying immediately, while heat vaporization systems first require appreciably heating the water.

Figure 2:
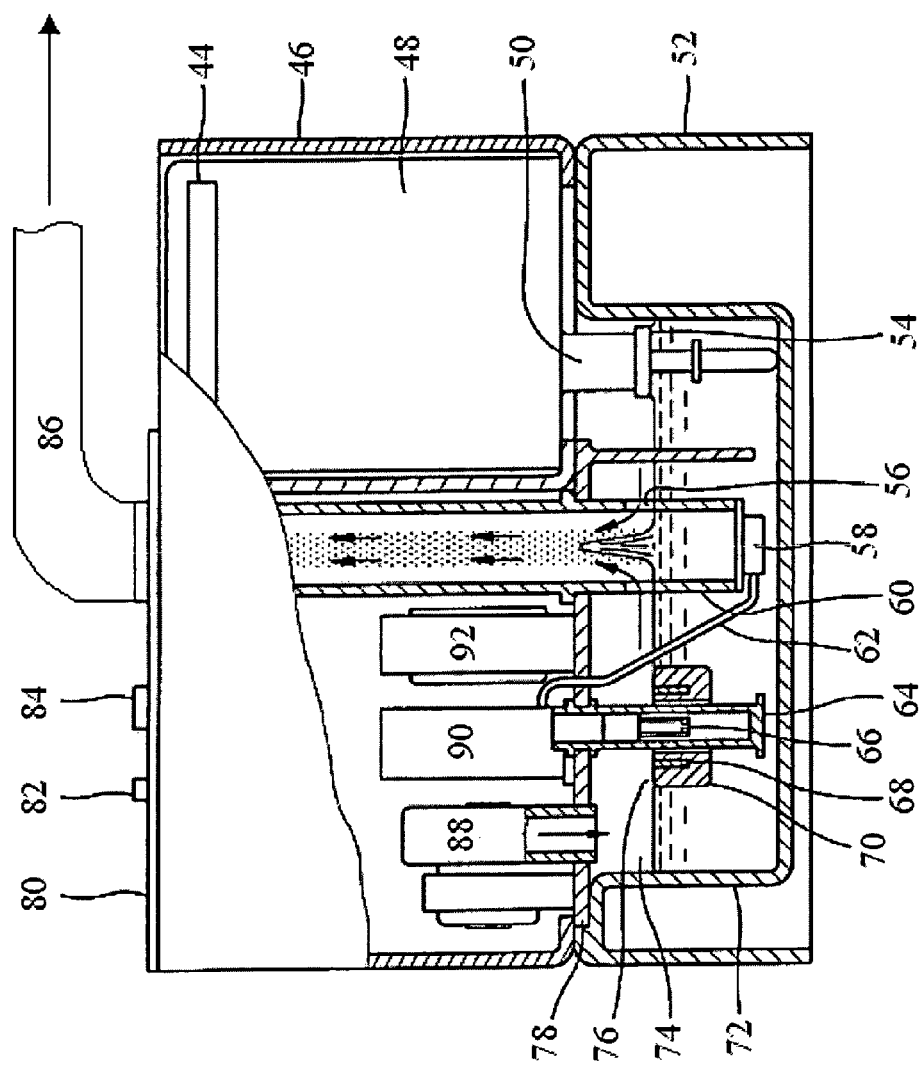
FIG. 2 is a diagram showing a preferred embodiment for an ultrasonic humidifier.

FIG. 2 shows a cross-section of an ultrasonic humidifier module which is the preferred embodiment for the present invention and can be incorporated or attached to the CPAP. Referring to FIG. 2, the ultrasonic humidifier has an upper cabinet 46 and a lower cabinet 52 which is arranged beneath upper cabinet 46. The bottom portion of upper cabinet 46 is open and lower cabinet 52 has a water vessel 72 which is integrally formed in the central portion of lower cabinet 52. Upper cabinet 46 and lower cabinet 52 are connected to each other through a chassis board 78.

A power transformer 92, a high frequency generator 90, and a motor-blower 88 are fixed on chassis board 78. Motor blower 88 supplies a space 74 in water vessel 72 with air from outside. The motor blower 88 can be replaced also by using the blower from the CPAP device. A low water detector 76 is suspended below the chassis board 78 so that the low water detector 76 protrudes into the water in water vessel 72. The low water detector 76 is magnetically operated. The low water detector 76 detects whether the level of water in water vessel 72 has fallen to below a predetermined value. The low water detector 76 comprises a float guide 64 which is perpendicularly fixed to chassis board 78 and extended in the downward direction, a magnetically operated switch 66 installed in float guide 64, and a float 70 having two bar magnets 68 inserted in float 70 therein. Float 70 is combined with float guide 64, to move upward and downward. When float 70 drops below the predetermined level of water according as the level of water in water vessel 72 has fallen, switch 66 is opened so high frequency generator 90 is stopped. When float 70 is in a position above the predetermined level, switch 66 is closed so high frequency generator 90 is operated.

A mist conduit pipe 60 which is comprised of an ultrasonic wave isolating material such as a plastic material is fixed to chassis board 78. The upper portion of mist conduit pipe 60 projects through upper cabinet 46 above upper cabinet 46, and the lower portion of mist conduit pipe 60 extends to near the bottom of water vessel 72 in lower cabinet 52. An outlet 86 is installed on the upper end of mist conduit pipe 60. An ultrasonic vibrator assembly 58 is fixed onto the lower end of mist conduit pipe 60. An ultrasonic vibrator (not shown) is installed in ultrasonic vibrator assembly 58. A plurality of holes 56 are formed in the lower peripheral portion of mist conduit pipe 60. Preferably, holes 56 are formed at the position just above the predetermined level of water in water vessel 72. A coaxial cable 62 for supplying the ultrasonic vibrator with high frequency energy is connected between high frequency generator 90 and ultrasonic vibrator assembly 58. A water supply tank 48 is removably placed in upper cabinet 46. The water supply tank 48 has an outlet pipe 50 projecting into water vessel 72, and a handle 94 for easily removing water supply tank 48 from upper cabinet 46.

A cap 54 having a valve mechanism is installed on the lower end of outlet pipe 50. The valve mechanism automatically supplies water vessel 72 with water to maintain the standard level determined by the lower end of cap 54. The upper cabinet 46 is covered with a top plate 80 except at the portion for mounting and removing water supply tank 48. A power switch 84 for keeping power transformer 92 or high frequency generator 90 operative or inoperative, and a lamp 82 kept lighted while power switch 84 is closed, keeping power transformer 92 and high frequency generator 90 operative, are provided on top plate 80.

When the water in water vessel 72 is positioned at the standard level, if power switch 84 is closed on, power transformer 92, high frequency generator 90, and motor blower 88 are in an operating state so a high frequency electric power will be fed to the ultrasonic vibrator through coaxial cable 62 from high frequency generator 90. Therefore, a high frequency energy generated from the ultrasonic vibrator is applied to the water in mist conduit pipe 60 to produce mist or water droplets smaller than 5 microns in diameter from the water in mist conduit pipe 60.

As shown by an arrow in FIG. 2, the air current fed into the space 74 of water vessel 72 by motor blower 88 flows into a mist conduit pipe 60 through holes 56 and is sprayed with the mist through outlet 86 into the flexible tubing 12 (see FIG. 1). When the water level in water vessel 72 lowers due to generating the mist, the pressure of the water vessel 72 is lowered. Thereby, the water in water supply tank 48 flows into water vessel 72 through outlet pipe 50 by the atmospheric pressure, so the water level recovers to the predetermined water level. If water supply tank 48 is removed, float 70 falls below the predetermined water level accordingly as the water level in water vessel 72 has fallen. In that case switch 66 is opened to stop the operation of high frequency generator 90 and motor blower 88. At the same time, a user is automatically alerted to the shortage of water in water vessel 72 by the lighting of a warning lamp.

When the water supply tank 48 is installed in upper cabinet 46 after the water supply tank 48 is filled with water, the water in water supply tank 48 flows into water vessel 72, so the water level in water vessel 72 recovers to the predetermined water level and switch 66 is closed to operate the humidifier.

Atomization can also be used to humidify the gas delivered to the subject. Atomization is a technique which produces droplets of liquid at a specific size and surface area. The most commonly utilized atomization techniques are pressure nozzle atomization, two-fluid nozzle atomization, and centrifugal atomization. In pressure nozzle atomization, a spray is created by forcing the fluid through an orifice. The energy required to overcome the pressure drop is supplied by a feed pump. This technique produces the narrowest particle size distribution possible. Droplet size can be controlled by altering the flow rate of the fluid through the atomizer. This is the most energy efficient atomization technique. Two-fluid nozzle atomization works by combining two fluids which are forced through a nozzle using a compressed gas. The atomization energy is provided by the compressed gas, usually air. The fluid contact can be internal or external to the nozzle. This technique produces a broad particle size distribution, and is the least energy efficient of the atomization techniques. This technique is useful for making extremely fine particles (10-30 micron) because of relatively high wear resistance. This technique is also useful for small flow rates typically found in pilot scale dryers. The initial cost can be lower due to the absence of a pressure pump, as found in pressure nozzle atomization, or a rotary atomizer, as found in centrifugal atomization. Centrifugal atomization creates a spray by passing the fluid across or through a rotary atomizer (a rotating wheel or disk). The energy required for atomization is supplied by the atomizer motor. A broad particle size distribution is generated. The average particle size for most products is no greater than 100 microns. Centrifugal atomizers are usually the most resistant to wear. This technique requires relatively high gas inlet velocity to prevent wall buildup. However, control of wall buildup is otherwise minimal, due to direction of spray (horizontal) and broad particle size distribution, forcing the dryer to be relatively large in diameter. The initial cost of a centrifugal atomizer is typically high. The comparatively larger diameter of the spray dryer can increase the initial cost. As with any high speed rotating machine, maintenance costs are also high. A problem with the centrifugal atomizer will shut down spray drying operations, unlike pressure nozzle atomization with multiple nozzle spray dryers, where a problem with one nozzle will not affect the operation of the other nozzles.

Figure 3:
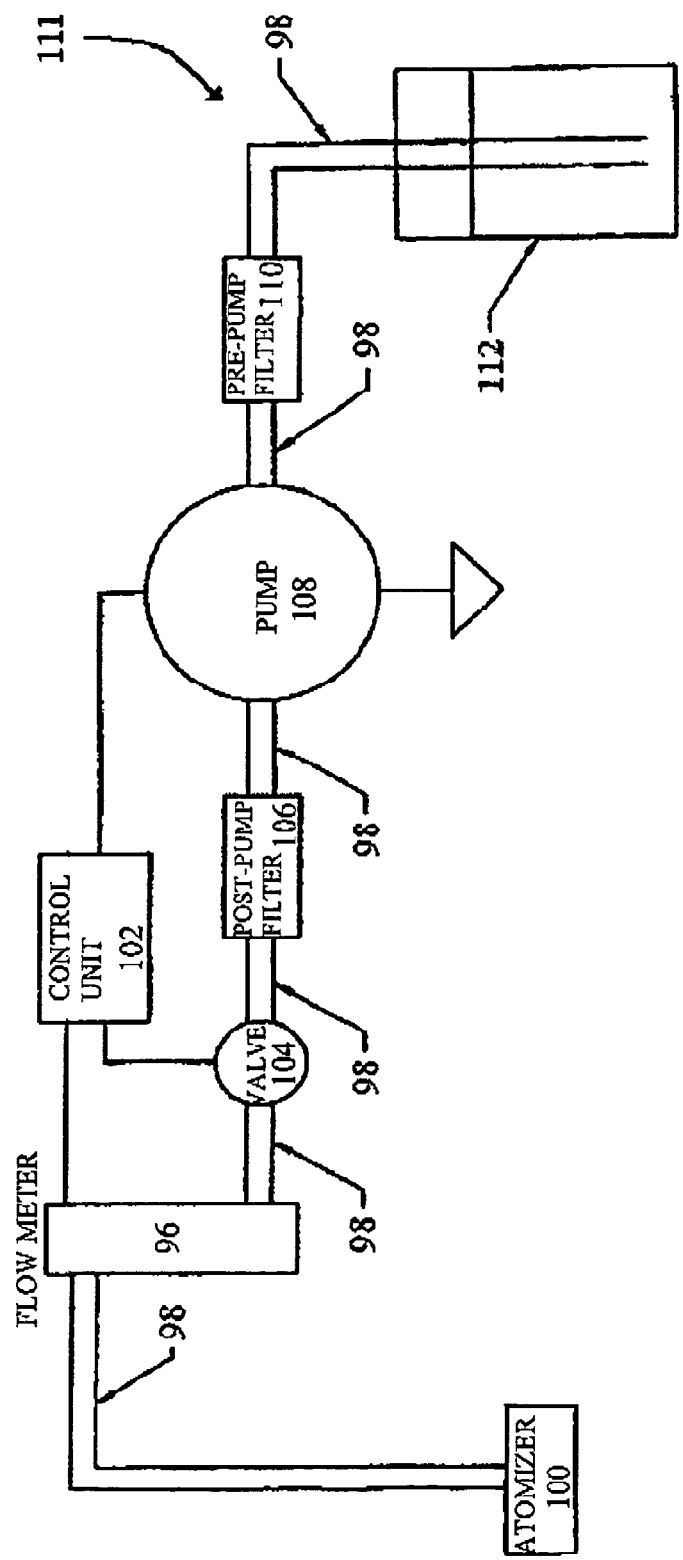
FIG. 3 is a schematic drawing of a generic liquid delivery system for an atomization humidifier.
Figure 4:
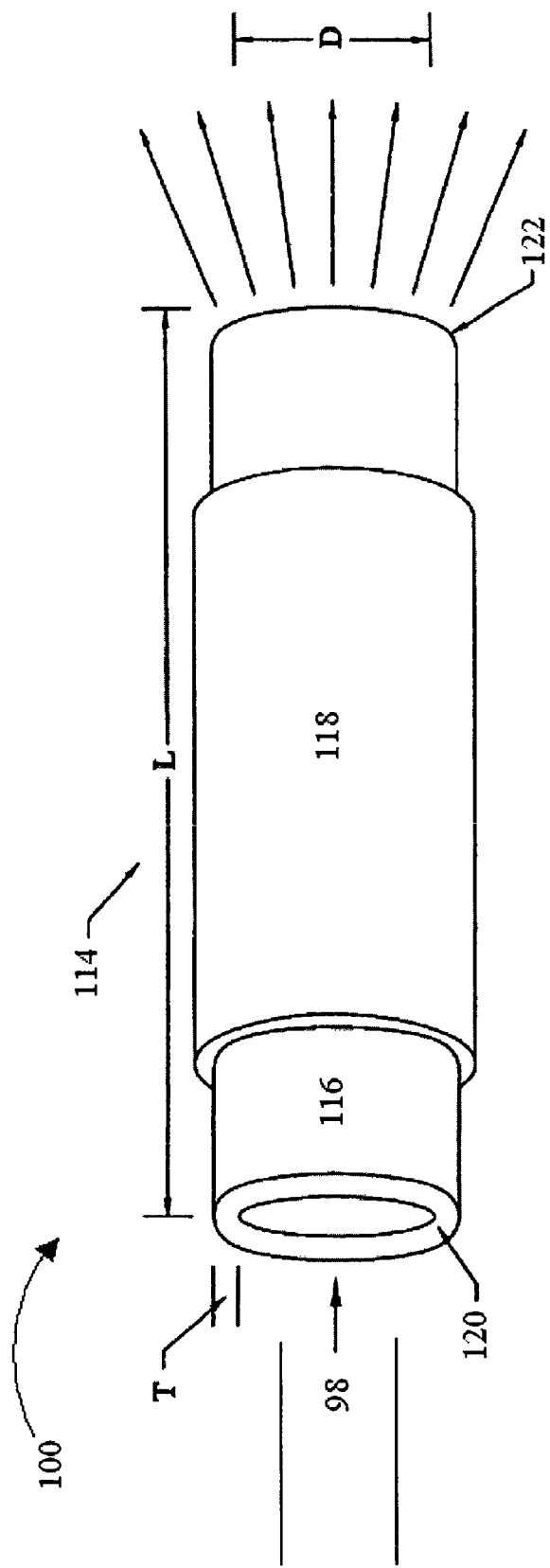
FIG. 4 is a detailed view of a preferred embodiment for an atomization humidifier.

FIGS. 3 and 4 show an embodiment of an atomizer module or attachment of the present invention. In FIG. 3 a generic liquid delivery system is indicated generally as 111. The delivery system 111 includes a liquid source 112 that contains the liquid to be delivered. A liquid supply line 98 supplies the liquid to the input of a pump 108 via a pre-pump filter 110. The pump 108 directs the liquid through a post-pump filter 106, a regulating valve 104, a flow meter 96, and finally to the input of the atomizer 100. An electronic control unit 102 receives input signals from the flow meter 96. Based on these feedback signals, the control unit 102 determines the appropriate power to deliver to the pump 108 to control the liquid flow rate. In addition, regulating valve 104 may be electronically adjustable so that the control unit 102 may control the liquid pressure "on-the-fly" should this be desired.

FIG. 4 shows a preferred embodiment of an atomization humidifier. This embodiment shows a pressure nozzle atomizer. This embodiment is basically a hollow tube 116 (shown here with a circular cross-section, although other shapes can be used), having a length L, an internal diameter D, a wall thickness T, an inlet end 120 and an outlet end 122. The material used in tube 116 is dependent on the overall size of the atomizer, liquid type, and other factors, although stainless steel has proved satisfactory. The physical mounting of the tube 116 can be provided by internal or external threaded portions of the tube 116, press fitting the tube or any other method that provides adequate strength while allowing liquid to freely flow therethrough.

In operation, liquid enters the inlet end 120 of the atomizer 114 from supply line 98. Upon exiting the outlet end of the tube 116, the pressure of the liquid drops rapidly, resulting in atomization of the liquid. The atomized liquid thereby produced is comprised of extremely small droplets (on the order of a few microns). A sleeve 118 of additional material may be installed over the entire length of tube 116 or only along a portion of the tube 116. The sleeve 118 can simply add structural strength to the atomizer 114, or may provide electrical and/or thermal insulation between the atomizer 114 and other apparatus components.

Nebulization can also be used to deliver humidified air in the CPAP of the present invention. A nebulizer changes liquids into fine droplets (in aerosol or mist form) that are inhaled through a mouthpiece or mask. Nebulizers can be used to deliver bronchodilator (airway-opening) medicines such as albuterol (Ventolin, Proventil or Airet) or ipratropium bromide (Atrovent). A nebulizer may be used instead of a metered dose inhaler. It is powered by a compressed air machine and plugs into an electrical outlet. Portable nebulizers, powered by an internal battery or cigarette lighter, are available for individuals requiring treatments away from home. Nebulizers come in 2 types: jet (or pneumatic) small-volume nebulizers, and ultrasonic nebulizers. Jet nebulizers pump air or oxygen, by means of an air compressor, through a liquid to turn it into a vapor, which is then inhaled through a tube-like mouthpiece similar to that of an inhaler. Ultrasonic nebulizers do not use air compressors but instead use sound vibrations to create the aerosol. The ultrasonic nebulizer humidifier is just another name for the ultrasonic humidifier, previously discussed. Both systems avoid contamination of the environment by the use of filters.

Figure 5:
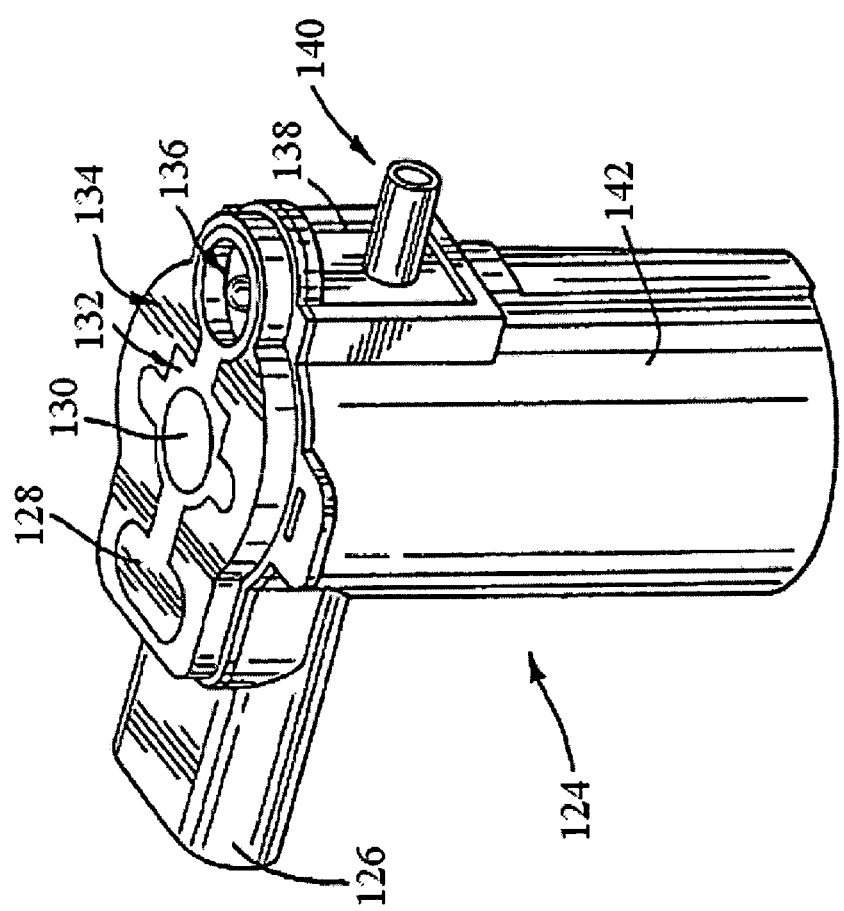
FIG. 5 is a diagram showing the exterior of a preferred embodiment for a nebulizer humidifier.
Figure 6:
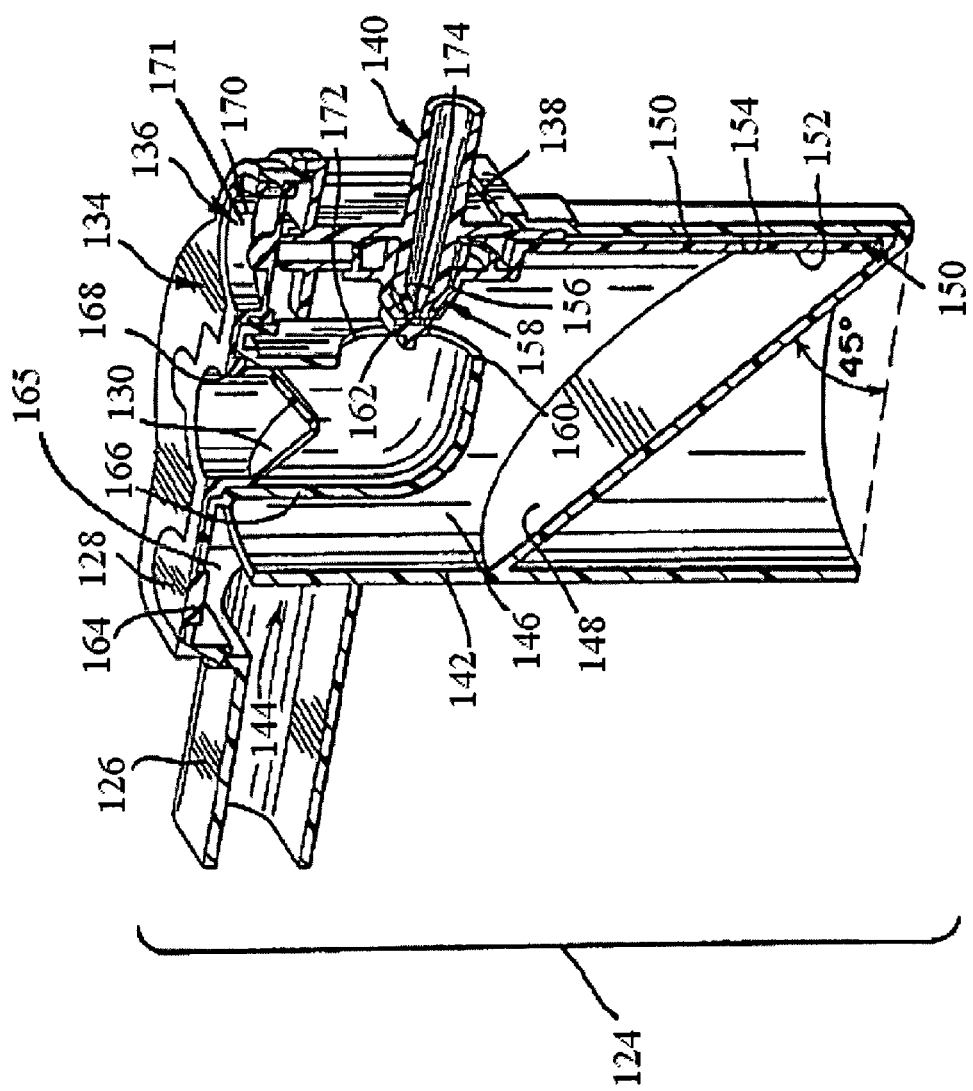
FIG. 6 is a diagram showing a cross-section of the same preferred embodiment for a nebulizer humidifier.

FIGS. 5 and 6 show an embodiment of a nebulizer humidifier module or attachment of the present invention. In FIGS. 5 and 6, the nebulizer humidifier module or attachment includes a housing 142 consisting of a chamber 146 that is suited to receive and hold a fluid. The chamber is preferably substantially cylindrical; however, any of a number of shapes may be used. The chamber 146 includes an angled bottom portion 148 so that any fluid in the chamber will be directed toward one region of the bottom of the chamber to facilitate removal of all the fluid. In one embodiment, the bottom portion 148 is set at an approximate 45 degree angle in order to reduce wastage by maximizing the amount of fluid that is evacuated from the chamber for nebulization. An air outlet 126 extends away from the housing 142 and communicates with the chamber 146. A bather 144 on the housing forces any aerosol generated in the chamber to flow up and over the barrier 144 before passing through the air outlet 126. The indirect path formed by the barrier and the air outlet preferably helps to limit the particle size of the aerosol that escapes the chamber 146.

Preferably, the housing is integrally formed with a lid portion 134 via a hinge 138 such that the lid portion 134 may be sealed and unsealed against the top of the housing to allow someone to fill the chamber 146 with a fluid. The lid portion 134 of the housing 142 is preferably molded as one part with the chamber 146.

The lid 134 preferably includes a group of openings suited to receive an air inlet valve 130, an exhalation valve 128 and a fluid channel air inlet valve 136, respectively. A first opening 165 is sized to accommodate the exhalation valve 128, a second opening 168 is sized to accommodate the air inlet valve 130, and the third opening 170 is sized to accommodate the fluid channel air inlet valve 136. The housing and lid may be constructed of a single piece of material formed by an injection molding process. Suitable materials include a plastic material, such as polypropylene, polycarbonate or a polycarbonate blend, or a metal material.

In a preferred embodiment, each of the air inlet valve 130, exhalation valve 128 and fluid channel air inlet valve 136 is integrally formed into a valve system 132 from a single piece of flexible material. The exhalation valve 128 preferably is mounted into the first opening 165 by a center anchor 164 so that the assembled valve and opening form a butterfly configuration allowing air to escape upon exhalation and sealing upon inhalation to prevent inhalation of air through the opening. The air inlet valve 130 preferably has a duck bill valve configuration. The duck bill valve configuration is oriented with the tapered portion directed into the chamber 146 so that ambient air may be drawn in upon inhalation and so that the parallel sealing members, or lips, of the valve prevent any flow of air out of the chamber upon exhalation. An ambient air guide 166 is preferably integrally formed in, or attached to, the lid portion 134. The ambient air guide 166 is disposed under the second opening 168 and the air inlet valve 130 so that distal opening 172 directs ambient air over the aerosol generating structure.

The fluid channel air inlet valve 136 preferably mounts into the third opening 170 and completely seals the third opening. Preferably, the fluid channel air inlet valve is a flexible membrane having a thickness that is sensitive to, and flexibly movable in response to, air pressure changes within the chamber 146 corresponding to inhalation and exhalation through the air outlet 126. The fluid channel air inlet 171 positioned inside the chamber and directly adjacent to the fluid channel air inlet valve may be sealed and unsealed synchronously with a patient's breathing or may be manually actuated by physical contact against the outside of the valve 30. In one embodiment, the material is flexible rubber material. Although individual valves may be fabricated separately on separate pieces of flexible material, or the valves may each be constructed from numerous individual components, the valve system 38 is preferably a one-piece, integrated construction reducing the part count and cost of manufacturing (including the cost of assembly).

A passageway 158 may be formed by a spacing between the gas nozzle 140 and nozzle cover 156, a groove in the inner circumference of the nozzle cover, a groove in the outside of the nozzle, or a combination of grooves on the outside of the nozzle and inside of the nozzle cover. The fluid orifice 160 is positioned adjacent the pressurized gas orifice 174. The fluid orifice is an annular orifice defined by a gap between the inner diameter of the tip of the nozzle cover and the outer diameter of the tip of the nozzle. In one preferred embodiment, the outer diameter of the tip of the nozzle is 2 mm and the inner diameter of the nozzle cover tip is 2.46 mm. Other diameters may also be used. Although a single annular orifice is shown, embodiments where the fluid outlet has other shapes, or comprises more than one discrete orifice positioned adjacent the pressurized gas orifice, are also contemplated.

In this embodiment, the fluid channel air inlet 171 is located near the top of the chamber 146 and is substantially parallel to the longitudinal axis of the chamber 146. The distal end of the nozzle cover forms a fluid orifice such that the fluid and gas orifices 160, 158 are substantially parallel to each other. The space between the nozzle cover 156 and the pressurized gas nozzle 140 forms the fluid passageway 158 at the distal end which leads to the fluid orifice 160. A non-moveable diverter 162 is located adjacent the distal end. The diverter directs the gas across the fluid orifice 160 to create a venturi effect, thereby causing the fluid to be entrained into the gas stream to create an aerosol. Preferably, the diverter 162 is attached to, or integrally molded with, the nozzle cover 156. Alternatively, the diverter may be connected to the inside of the nebulizer 124.

The fluid channel stem 152 extends substantially vertically along the longitudinal axis of the chamber 146. The stem has a carved out portion 150 which forms an enclosed lumen once it is assembled and mated with the recessed channel 154 in the chamber wall. The resulting fluid channel shape is substantially rectangular. In other embodiments, the recessed channel 154 and carved-out portion 150 of the fluid channel stem 152 may be constructed to cooperate and form any of a number of continuous or varying cross-sections along their lengths. In another embodiment, the recessed channel 154 and fluid channel stem 152 may combine to form a plurality of separate fluid channels. In one preferred embodiment, the chamber has a volume of approximately 50 milliliters (ml), with a maximum fluid fill volume of 5 ml. In this embodiment, the fluid channel length is approximately 22.8 mm.

The fluid channel air inlet valve 136 is a flexible membrane that on inhalation substantially seals the fluid channel air inlet 171 communicating with the fluid inlet tube. Once substantially sealed, the necessary pressure is created inside the housing in order to entrain the fluid up the fluid channel into the path of the pressurized gas causing the fluid and gas to mix resulting in an aerosol with the desired particle size characteristics. The flexible membrane is preferably very sensitive to flow and, therefore, can be triggered at low flows making the apparatus suitable for children and the elderly who typically have lower rates of inhalation. Further, the membrane can also be manually depressed. Accordingly, the patient or the caregiver can manually actuate the apparatus.

A nebulizer capable of both breath actuation and manual actuation has been disclosed where a diverter, gas orifice, and liquid orifice are maintained in a fixed position with one another at all times. Nebulization is initiated by movement of a valve over the fluid channel air inlet that is in communication with the fluid channel linking the liquid orifice with the reservoir in the chamber. By using a flexible membrane as the fluid channel air inlet valve, a very fast and reliable response to both increased and decreased pressures within the chamber of the nebulizer may be realized.

The present invention also contemplates devices such as impellers and other non-heat active-force humidifiers for use as the humidification module for the CPAP device.

Figure 7:
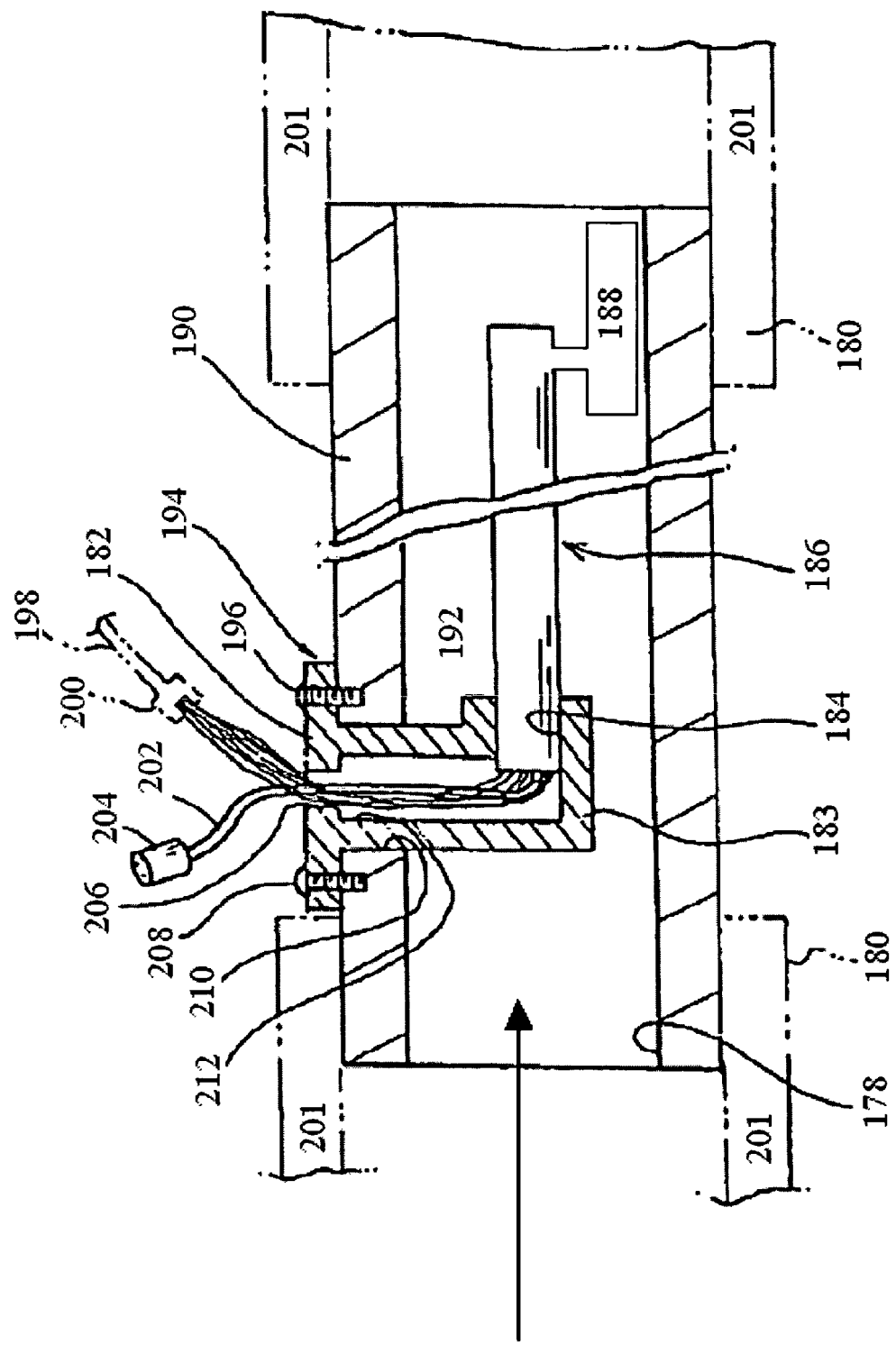
FIG. 7 is a diagram detailing the preferred device for removing condensation from the humidified air, which includes the condensation coil or membrane and surrounding components.

Optionally, for any humidifier covered by the present invention, we can include a condensation coil (condensation membrane) droplet filter within the humidification device. This device can be used to remove larger droplets of water to ensure reduced condensation between the humidifier and subject interface. In a preferred embodiment, shown in FIG. 7, patient circuit 201 is mounted detachably to the humidification unit 192 that is provided with a short connection tube 190 as a support member, a mounting flange 194, and a humidifying element 186. Connection tube 190 may be a straight tube with both end portions engaged (connected) in an airtight fashion to connection end portions 180 of patient circuit 201. The outer diameter of connection tube 190 is set so as to be somewhat larger than the inner diameter of patient circuit 201, in order to ensure the airtight engagement with patient circuit 192 to be connected thereto, and it may be set appropriately in accordance with the patient circuit to be employed. Further, in this case, the use of a packing, a fastening band or the like may be employed in order to enhance airtightness.

The peripheral wall on one end of connection tube 190 (e.g., on the left side in FIG. 7) is formed with a mounting opening 210 for mounting flange 194. Mounting opening 210 is located at a position outside of connection end portion 180 of patient circuit 201 upon connection with connection end portion 180 and disposed so as to allow the inside of connection tube 190 to communicate with the outside thereof.

In the illustrated exemplary embodiment, mounting flange 194 consists of a flange portion 182 in a square-plate shape or the like and a cylindrical holding portion 183. Flange portion 182 of mounting flange 194 is shaped so as to be disposed along an outer peripheral wall of connection tube 190 and it is fixed to connection tube 190 by a screw 196 so as to cover the mounting opening 210 of connection tube 190 in a tight manner. Flange portion 182 is further provided with a communicating opening 206 that allows mounting opening 210 of connection tube 190 to open to the outside in the center of flange portion 182.

Holding portion 183 of mounting flange 194 is disposed so as to stand upright with respect to the plate surface of flange portion 182, such that opening 206 of flange portion 182 faces an opening 212 at the base end thereof. Holding portion 183 is arranged so as to insert through mounting opening 210 of connection tube 190 over the entire length of mounting opening 210 of connection tube 190, extending up to the center of connection tube 190 in the radial direction, and then curved on the other end side of connection tube 190 at a generally right angle (on the right end side in FIG. 7). An opening 184 is defined in holding portion 183 so as to face an open end of connection tube 190. Opening 184 at one end of holding portion 183 is large enough to engage and hold humidifying element 186, and opening 184 is arranged so as to communicate to the outside through communicating opening 206 of flange portion 6a in holding portion 183.

In a preferred embodiment, the humidifying element 186 consists of a cylindrical bundle of tubes through which the humidified air stream passes. Each tube in the bundle is comprised of pores large enough to allow certain size vapor particles to pass through but small enough to keep in larger size particles. These larger liquid particles collect as condensation, which are collected in reservoir 188. Preferably, the pores are small enough to trap liquid particles in the air larger than 10 microns in diameter. However, the pore size can be adjusted to best suit the needs of the patient. Preferably, the water in the reservoir 188 may be recycled back to the corresponding humidifier holding tank (depending on which non-heat, active-force humidifier is used) or may be disposed of in any other feasible manner.

An alternative to the condensation coil or membrane could be a condensation reservoir 44, which would be attached to flexible tubing 12 between flow-resistive element 6 and the mask 4, all shown in FIG. 1. This reservoir would collect any condensation forming present in the flexible tubing 12 before it could reach the humidifier and subject interface. The collected water could then be recycled back to the humidification module or disposed of by any other manner. A preferred embodiment for the reservoir may include a wall extending from the bottom of the flexible tubing 12 on the subject 2 side of the reservoir to partially obstruct the tube and to block any liquid from progressing further down the tube and thus forcing it to fall into the reservoir. In this embodiment, the reservoir would be lower than the flexible tubing 12 to allow gravity to pull the condensation into the reservoir after hitting the wall. The reservoir may be attached to the flexible tubing 12 by means of another tube or by any other means, including a spout or funnel.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A continuous positive airway pressure apparatus for treating sleep apneas comprising
    a device for pressurizing gas to treat a subject for sleep apnea;
    a humidifier integrated into the device for actively humidifying a gas without substantially heating the humidified gas prior to delivery to the subject; and
    a tube connected to the device, and a mask or a cannula connected to the tube for delivering the humidified, pressurized gas from the device to the subject
    wherein any condensation from the humidified air is collected and substantially removed from the paths of the humidified and/or pressurized gas by the use of a condensation coil or membrane located within the device for actively humidifying the gas, and the condensation coil or membrane comprises one or more cylindrical tubes containing pores of a number of sizes, through which gas particles and liquid particles smaller than the size of the pores may pass.

2. The apparatus in claim 1, wherein the condensation collected in the condensation coil is collected in a reservoir.

* * * * *